US012403588B2

United States Patent
Palaniswamy et al.

(10) Patent No.: US 12,403,588 B2
(45) Date of Patent: Sep. 2, 2025

(54) ARTIFICIAL MUSCLES COMPRISING A PARTIALLY INSULATED ELECTRODE PAIR AND METHODS FOR OPTIMIZING VOLTAGE POLARITY CONDITIONS IN THE ARTIFICIAL MUSCLES

(71) Applicant: Toyota Motor Engineering & Manufacturing North America, Inc., Plano, TX (US)

(72) Inventors: Maduran Palaniswamy, Ann Arbor, MI (US); Michael P. Rowe, Pinckney, MI (US); Max P. Herzog, Fenton, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 854 days.

(21) Appl. No.: 17/685,504

(22) Filed: Mar. 3, 2022

(65) Prior Publication Data
US 2023/0173663 A1 Jun. 8, 2023

Related U.S. Application Data

(60) Provisional application No. 63/285,707, filed on Dec. 3, 2021.

(51) Int. Cl.
*F15B 15/10* (2006.01)
*B25J 9/10* (2006.01)
(Continued)

(52) U.S. Cl.
CPC ............ *B25J 9/1075* (2013.01); *B25J 9/142* (2013.01); *F15B 15/103* (2013.01); *A61F 2002/0894* (2013.01)

(58) Field of Classification Search
CPC ........ B25J 9/1075; B25J 9/142; F15B 15/103; F15B 15/10; F15B 21/06; F15B 2211/885;
(Continued)

(56) References Cited

U.S. PATENT DOCUMENTS

2020/0032822 A1* 1/2020 Keplinger ............... F15B 21/06
2020/0132213 A1* 4/2020 Gandhi .................. H02N 1/006
(Continued)

FOREIGN PATENT DOCUMENTS

JP 5144096 B2 2/2013
KR 20080028148 A 3/2008
(Continued)

OTHER PUBLICATIONS

Kyung et al, Pouch Type Soft Actuator with Hetero Space Change Layer and Dielectric Fluid, Jul. 8, 2021, KR 20210086518 (English Machine Translation) (Year: 2021).*
(Continued)

*Primary Examiner* — Alexander A Singh
(74) *Attorney, Agent, or Firm* — Dinsmore & Shohl LLP

(57) ABSTRACT

An artificial muscle system includes an artificial muscle and a power supply. The artificial muscle includes an electrode pair including a first electrode and a second electrode, an electrical insulator membrane fixed to the second electrode, a housing including an electrode region and an expandable fluid region, the electrode pair positioned in the electrode region of the housing, and a dielectric fluid housed within the housing. The power supply includes a positive terminal and a negative terminal. The positive terminal is electrically coupled to the second electrode. The negative terminal is electrically coupled to the first electrode. The electrode pair is actuatable between a non-actuated state and an actuated state such that actuation from the non-actuated state to the
(Continued)

actuated state directs the dielectric fluid into the expandable fluid region.

19 Claims, 6 Drawing Sheets

(51) Int. Cl.
 *B25J 9/14* (2006.01)
 *A61F 2/08* (2006.01)

(58) Field of Classification Search
 CPC ........... F15B 2215/305; F03G 7/06324; F03G 7/0121; A61F 2002/0894
 USPC ........................................................ 310/309
 See application file for complete search history.

(56) References Cited

U.S. PATENT DOCUMENTS

2021/0369547 A1 12/2021 Mau et al.
2021/0370499 A1* 12/2021 Rowe .................... F15B 21/065

FOREIGN PATENT DOCUMENTS

| KR | 20080028171 A | | 3/2008 |
|---|---|---|---|
| KR | 20210086518 A | * | 7/2021 |
| WO | 2008035732 A1 | | 3/2008 |

OTHER PUBLICATIONS

E. Acome et al. "Hydraulically amplified self-healing electrostatic actuators with muscle-like performance", Science Jan. 5, 2018: vol. 359, Issue 6371, pp. 61-65.

* cited by examiner

ARTIFICIAL MUSCLES COMPRISING A PARTIALLY INSULATED ELECTRODE PAIR AND METHODS FOR OPTIMIZING VOLTAGE POLARITY CONDITIONS IN THE ARTIFICIAL MUSCLES

CROSS-REFERENCE TO RELATED APPLICATION

This application claims the priority benefit of U.S. Provisional Patent Application No. 63/285,707, filed Dec. 3, 2021, for "Artificial Muscles Comprising A Partially Insulated Electrode Pair And Methods For Optimizing Voltage Polarity Conditions In The Artificial Muscles," which is hereby incorporated by reference in its entirety including the drawings.

TECHNICAL FIELD

The present specification generally relates to apparatus and methods for focused inflation on at least one surface of a device, and, more specifically, apparatus and methods for utilizing an electrode pair to direct a fluid to inflate the device.

BACKGROUND

Current robotic technologies rely on rigid components, such as servomotors to perform tasks, often in a structured environment. This rigidity presents limitations in many robotic applications, caused, at least in part, by the weight-to-power ratio of servomotors and other rigid robotics devices. The field of soft robotics improves on these limitations by using artificial muscles and other soft actuators. Artificial muscles attempt to mimic the versatility, performance, and reliability of a biological muscle. Some artificial muscles rely on fluidic actuators, but fluidic actuators require a supply of pressurized gas or liquid, and fluid transport must occur through systems of channels and tubes, limiting the speed and efficiency of the artificial muscles. Other artificial muscles use thermally activated polymer fibers, but these are difficult to control and operate at low efficiencies. Additionally, electrically coupling a non-insulated electrode to a positive terminal of a power supply may result in a chemical buildup, e.g., oligomerization, on the exposed surface of the non-insulated electrode in contact with a dielectric fluid. This chemical buildup may result in operation failure of the artificial muscle.

Accordingly, a need exists for improved artificial muscles that are electrically coupled to a power supply in a particular manner based on whether an electrical insulator layer is provided on one or both of the electrodes of the artificial muscles.

SUMMARY

In one embodiment, an artificial muscle system includes an artificial muscle and a power supply. The artificial muscle includes an electrode pair including a first electrode and a second electrode, an electrical insulator membrane fixed to a surface of the second electrode facing the first electrode, a housing including an electrode region and an expandable fluid region, the electrode pair positioned in the electrode region of the housing, the first electrode fixed to a first surface of the housing and the second electrode fixed to a second surface of the housing, and a dielectric fluid housed within the housing. The power supply includes a positive terminal and a negative terminal. The positive terminal is electrically coupled to the second electrode. The negative terminal is electrically coupled to the first electrode. The electrode pair is actuatable between a non-actuated state and an actuated state such that actuation from the non-actuated state to the actuated state directs the dielectric fluid into the expandable fluid region.

In another embodiment, an artificial muscle system including an artificial muscle and a power supply. The artificial muscle includes an electrode pair including a first electrode and a second electrode, the first electrode and the second electrode each including a plurality of electrode segments, an electrical insulator membrane fixed to one or more electrode segments of the first electrode and one or more corresponding electrode segments of the second electrode, a housing comprising an electrode region and an expandable fluid region, the electrode pair positioned in the electrode region of the housing, the first electrode fixed to a first surface of the housing and the second electrode fixed to a second surface of the housing, and a dielectric fluid housed within the housing. The power supply includes a positive terminal and a negative terminal, the positive terminal electrically coupled to the one or more electrode segments of the first electrode and the one or more corresponding electrode segments of the second electrode, the negative terminal electrically coupled to one or more other electrode segments of the first electrode and one or more other electrode segments of the second electrode. The electrode pair is actuatable between a non-actuated state and an actuated state such that actuation from the non-actuated state to the actuated state directs the dielectric fluid into the expandable fluid region.

In yet another embodiment, a method for actuating an artificial muscle includes electrically coupling a negative terminal and a positive terminal of a power supply to an electrode pair of the artificial muscle. The artificial muscle includes a housing having an electrode region and an expandable fluid region. The electrode pair includes a first electrode electrically coupled to the negative terminal of the power supply, and a second electrode electrically coupled to the positive terminal of the power supply, the electrode pair positioned in the electrode region of the housing. An electrical insulator membrane is fixed to the second electrode. The method further includes applying a voltage from the power supply to the electrode pair of the artificial muscle, thereby actuating the electrode pair from a non-actuated state to an actuated state such that dielectric fluid is directed into the expandable fluid region of the housing and expands the expandable fluid region.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
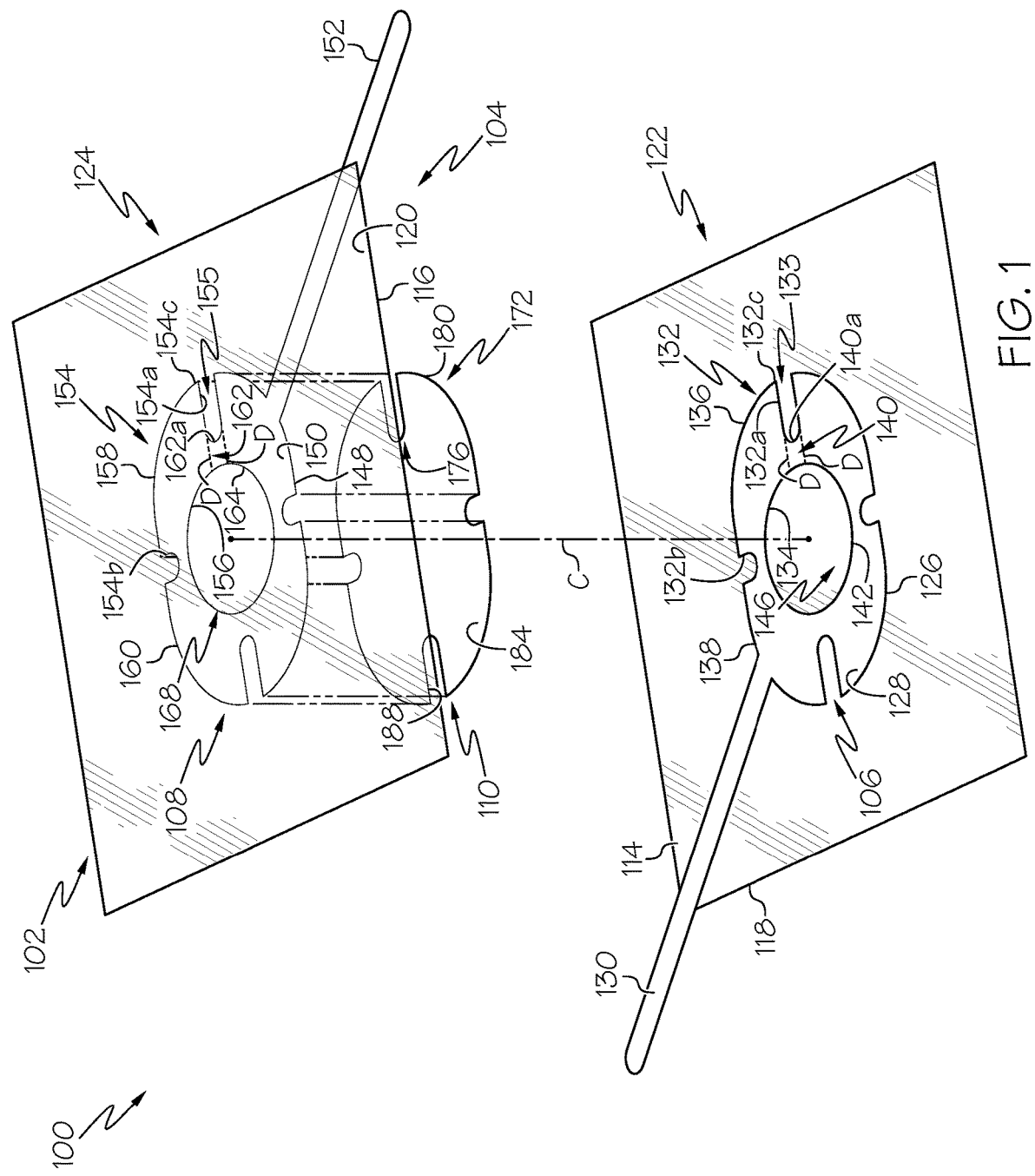
FIG. 1 schematically depicts an exploded view of an artificial muscle, according to one or more embodiments shown and described herein.

Embodiments described herein are directed to artificial muscles and artificial muscle assemblies electrically coupled to a power supply. The artificial muscles described herein are actuatable to selectively raise and lower a region of the artificial muscles to provide a selective, on demand inflated expandable fluid region. The artificial muscles include a housing and an electrode pair. A dielectric fluid is housed within the housing, and the housing includes an electrode region and an expandable fluid region, where the electrode pair is positioned in the electrode region. The electrode pair includes a first electrode and a second electrode. The electrode pair is actuatable between a non-actuated state and an actuated state such that actuation from the non-actuated state to the actuated state directs the dielectric fluid into the expandable fluid region. This expands the expandable fluid region, raising a portion of the artificial muscle on demand. Various embodiments of the artificial muscles and the operation of the artificial muscles are described in more detail herein. Whenever possible, the same reference numerals will be used throughout the drawings to refer to the same or like parts.

Figure 2:
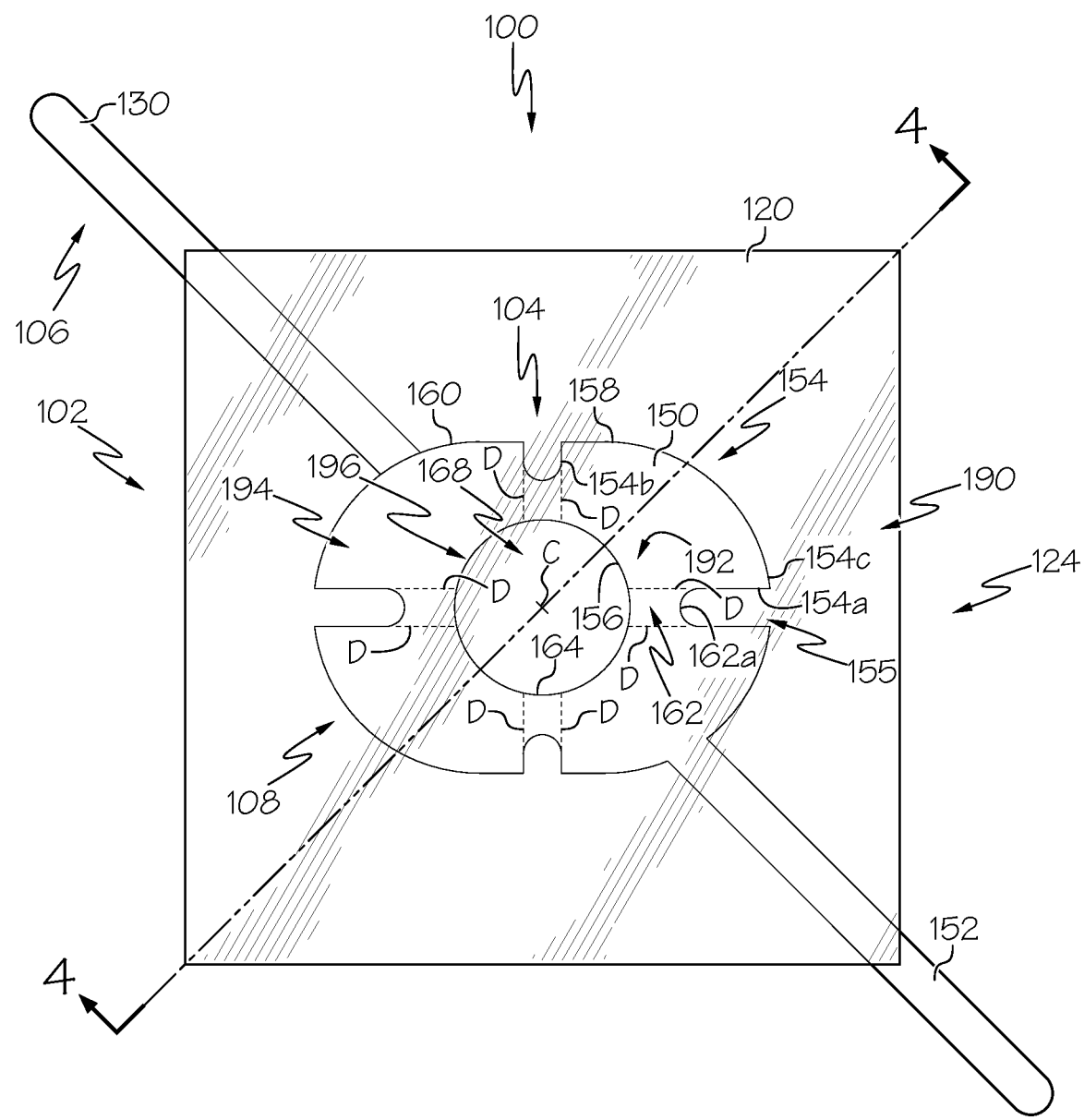
FIG. 2 schematically depicts a top view of the artificial muscle of FIG. 1, according to one or more embodiments shown and described herein.

Referring now to FIGS. 1 and 2, an artificial muscle 100 is shown. The artificial muscle 100 includes a housing 102, an electrode pair 104, including a first electrode 106 and a second electrode 108, fixed to opposite surfaces of the housing 102, and an electrical insulator membrane 110 fixed to the second electrode 108. It should be appreciated that the first electrode 106 remains uninsulated. However, in embodiments, a second electrical insulator membrane may be fixed to the first electrode 106 to electrically insulate the first electrode 106.

Figure 9:
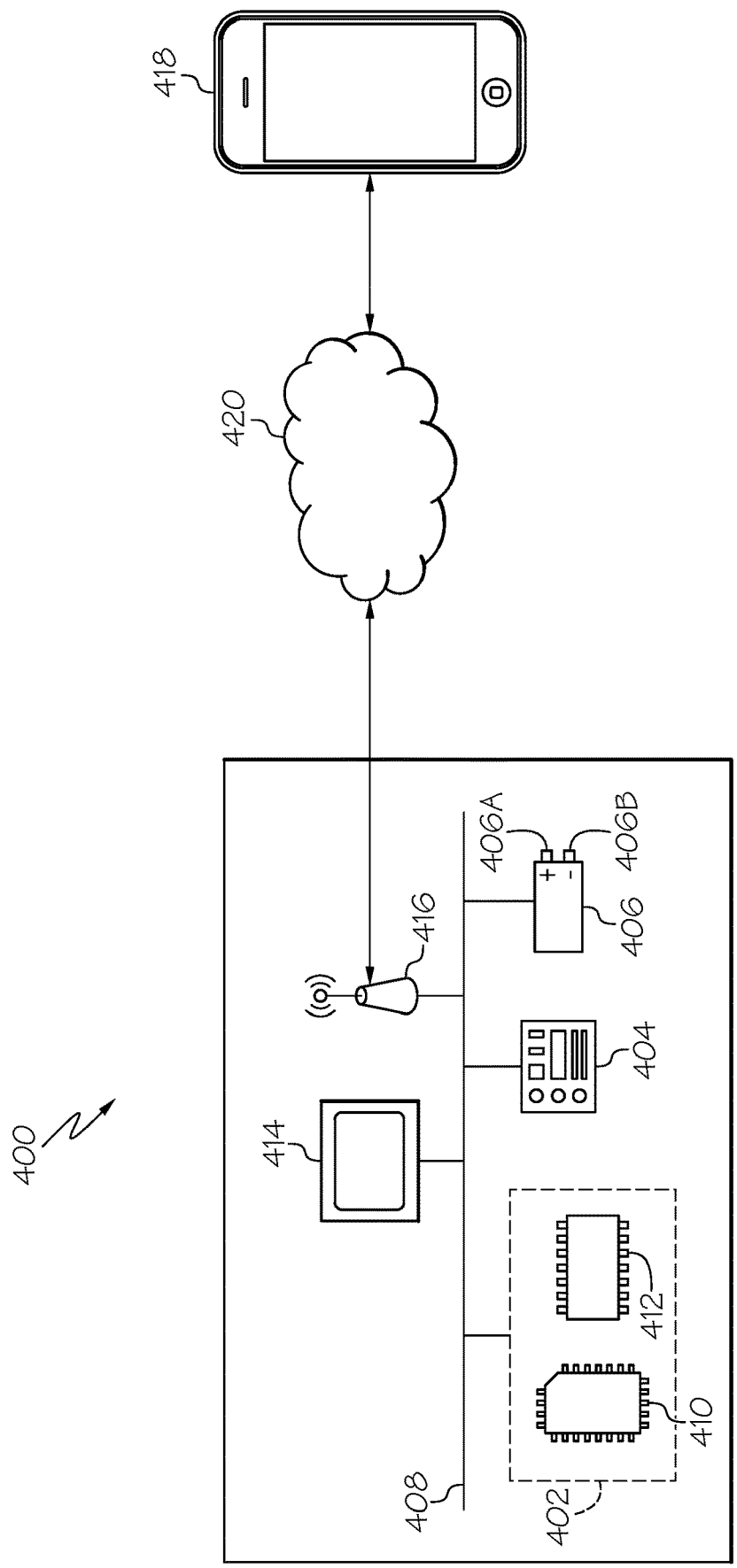
FIG. 9 schematically depicts an actuation system for operating an artificial muscle, according to one or more embodiments shown and described herein.

As discussed in more detail herein, the second electrode 108, which receives the electrical insulator membrane 110, is to be electrically coupled or electrically connected to a positive terminal of a power supply, such as a positive terminal 406A of a power supply 406 (FIG. 9). Accordingly, the first electrode 106, which does not receive the electrical insulator membrane 110, is to be electrically coupled or electrically connected to a negative terminal of a power supply, such as a negative terminal 406B of the power supply 406 (FIG. 9). Although the electrical insulator membrane 110 is described herein as being fixed to the second electrode 108, it should be appreciated that, in embodiments, the electrical insulator membrane 110 may alternatively be fixed to the first electrode 106. In this embodiment, the first electrode 106 would be electrically coupled to the positive terminal of the power supply, and the second electrode 108 would be electrically coupled to the negative terminal of the power supply.

As referred to herein, reference to a "negative terminal" of a power supply refers to the negatively charged electrode of a power supply from which the electrons emerge, which may commonly be referred to as a "cathode." Similarly, as referred to herein, reference to a "positive terminal" of a power supply refers to the positively charged electrode of a power supply that receives electrons, which may commonly be referred to as a "anode."

In some embodiments, the housing 102 is a one-piece monolithic layer including a pair of opposite inner surfaces, such as a first inner surface 114 and a second inner surface 116, and a pair of opposite outer surfaces, such as a first outer surface 118 and a second outer surface 120. In some embodiments, the first inner surface 114 and the second inner surface 116 of the housing 102 are heat-sealable. In other embodiments, the housing 102 may be a pair of individually fabricated film layers, such as a first film layer 122 and a second film layer 124. Thus, the first film layer 122 includes the first inner surface 114 and the first outer surface 118, and the second film layer 124 includes the second inner surface 116 and the second outer surface 120.

Throughout the ensuing description, reference may be made to the housing 102 including the first film layer 122 and the second film layer 124, as opposed to the one-piece housing. It should be understood that either arrangement is contemplated. In some embodiments, the first film layer 122 and the second film layer 124 generally include the same structure and composition. For example, in some embodiments, the first film layer 122 and the second film layer 124 each comprises biaxially oriented polypropylene (BOPP).

The first electrode 106 and the second electrode 108 are each positioned between the first film layer 122 and the second film layer 124. In some embodiments, the first electrode 106 and the second electrode 108 are each aluminum-coated polyester such as, for example, Mylar®. In addition, one of the first electrode 106 and the second electrode 108 is a negatively charged electrode and the other of the first electrode 106 and the second electrode 108 is a positively charged electrode. For purposes discussed herein, either electrode 106, 108 may be positively charged so long as the other electrode 106, 108 of the artificial muscle 100 is negatively charged.

The first electrode 106 has a film-facing surface 126 and an opposite inner surface 128. The first electrode 106 is positioned against the first film layer 122, specifically, the first inner surface 114 of the first film layer 122. In addition, the first electrode 106 includes a first terminal 130 extending from the first electrode 106 past an edge of the first film layer 122 such that the first terminal 130 can be connected to a power supply to actuate the first electrode 106. Specifically, the terminal 130 is coupled, either directly or in series, to a power supply and a controller of an actuation system 400, as shown in FIG. 9. Similarly, the second electrode 108 has a film-facing surface 148 and an opposite inner surface 150. The second electrode 108 is positioned against the second film layer 124, specifically, the second inner surface 116 of the second film layer 124. The second electrode 108 includes a second terminal 152 extending from the second electrode 108 past an edge of the second film layer 124 such that the second terminal 152 can be connected to a power supply and a controller of the actuation system 400 to actuate the second electrode 108.

It should be appreciated that the second terminal 152, which extends from the second electrode 108 that is electrically insulated by the electrical insulator membrane 110, is electrically coupled to the positive terminal 406A of the power supply 406 (FIG. 9). Additionally, the first terminal 130, which extends from the first electrode 106 that is not electrically insulated (non-insulated), is electrically coupled to a negative terminal 406B of the power supply 406 (FIG. 9).

By electrically coupling the insulated electrode, i.e., the second electrode 108, to the positive terminal 406A of the power supply 406, a chemical buildup, e.g., oligomerization, on the non-insulated electrode, i.e., the first electrode 106, is reduced. It should be appreciated that in in instances in which a non-insulated electrode is connected to a positive terminal of a power supply, the dielectric fluid, such as dielectric fluid 198, will build up on the non-insulated electrode and create a "scum" layer on the exposed, non-insulated surface of the electrode.

In the present embodiment, the positive terminal 406A of the power supply 406 is electrically coupled to the second electrode 108. However, it should be appreciated that, in other embodiments, the first electrode 106 may be insulated by the electrical insulator membrane 110, thereby leaving the second electrode 108 non-insulated. In this embodiment, the first electrode 106 would be electrically coupled to the positive terminal 406A of the power supply 406 and the second electrode 108 would be electrically coupled to the negative terminal 406B of the power supply 406.

With respect now to the first electrode 106, the first electrode 106 includes two or more fan portions 132 extending radially from a center axis C of the artificial muscle 100. In some embodiments, the first electrode 106 includes only two fan portions 132 positioned on opposite sides or ends of the first electrode 106. In some embodiments, the first electrode 106 includes more than two fan portions 132, such as three, four, or five fan portions 132. In embodiments in which the first electrode 106 includes an even number of fan portions 132, the fan portions 132 may be arranged in two or more pairs of fan portions 132. As shown in FIG. 1, the first electrode 106 includes four fan portions 132. In this embodiment, the four fan portions 132 are arranged in two pairs of fan portions 132, where the two individual fan portions 132 of each pair are diametrically opposed to one another.

Each fan portion 132 has a first side edge 132a and an opposite second side edge 132b. As shown, the first terminal 130 extends from the second end 136 of one of the fan portions 132 and is integrally formed therewith. A channel 133 is at least partially defined by opposing side edges 132a, 132b of adjacent fan portions 132 and, thus, extends radially toward the center axis C. The channel 133 terminates at an end 140a of a bridge portion 140 interconnecting adjacent fan portions 132.

As shown in FIG. 1, dividing lines D are included to depict the boundary between the fan portions 132 and the bridge portions 140. The dividing lines D extend from the side edges 132a, 132b of the fan portions 132 to the first end 134 of the fan portions 132 collinear with the side edges 132a, 132b. It should be understood that dividing lines D are shown in FIG. 1 for clarity and that the fan portions 132 are integral with the bridge portions 140. The first end 134 of the fan portion 132, which extends between adjacent bridge portions 140, defines an inner length of the fan portion 132. Due to the geometry of the fan portion 132 tapering toward the center axis C between the first side edge 132a and the second side edge 132b, the second end 136 of the fan portion 132 defines an outer length of the fan portion 132 that is greater than the inner length of the fan portion 132.

Moreover, each fan portion 132 has a pair of corners 132c defined by an intersection of the second end 136 and each of the first side edge 132a and the second side edge 132b of the fan portion 132. In embodiments, the corners 132c are formed at an angle equal to or less than 90 degrees. In other embodiments, the corners 132c are formed at an acute angle.

As shown in FIG. 1, each fan portion 132 has a first side length defined by a distance between the first end 134 of the fan portion 132 and the second end 136 of the fan portion 132 along the first side edge 132a and the dividing line D that is collinear with the first side edge 132a. Each fan portion 132 also has a second side length defined by a distance between the first end 134 of the fan portion 132 and the second end 136 of the fan portion 132 along the second side edge 132b and the dividing line D that is collinear with the second side edge 132b. In embodiments, the first side length is greater than the second side length of the fan portion 132 such that the first electrode 106 has an ellipsoid geometry.

The second end 136, the first side edge 132a and the second side edge 132b of each fan portion 132, and the bridge portions 140 interconnecting the fan portions 132 define an outer perimeter 138 of the first electrode 106. In embodiments, a central opening 146 is formed within the first electrode 106 between the fan portions 132 and the bridge portions 140, and is coaxial with the center axis C. Each fan portion 132 has a fan length extending from a perimeter 142 of the central opening 146 to the second end 136 of the fan portion 132. Each bridge portion 140 has a bridge length extending from a perimeter 142 of the central opening 146 to the end 140a of the bridge portion 140, i.e., the channel 133. As shown, the bridge length of each of the bridge portions 140 is substantially equal to one another. Each channel 133 has a channel length defined by a distance between the end 140a of the bridge portion 140 and the second end of the fan portion 132. Due to the bridge length of each of the bridge portions 140 being substantially equal to one another and the first side length of the fan portions 132 being greater than the second side length of the fan portions 132, a first pair of opposite channels 133 has a channel length greater than a channel length of a second pair of opposite channels 133. As shown, a width of the channel 133 extending between opposing side edges 132a, 132b of adjacent fan portions 132 remains substantially constant due to opposing side edges 132a, 132b being substantially parallel to one another.

In embodiments, the central opening 146 has a radius of 2 centimeters (cm) to 5 cm. In embodiments, the central opening 146 has a radius of 3 cm to 4 cm. In embodiments, a total fan area of each of the fan portions 132 is equal to or greater than twice an area of the central opening 146. It should be appreciated that the ratio between the total fan area of the fan portions 132 and the area of the central opening 146 is directly related to a total amount of deflection of the first film layer 122 when the artificial muscle 100 is actuated, as discussed herein. In embodiments, the bridge length is 20% to 50% of the fan length. In embodiments, the bridge length is 30% to 40% of the fan length. In embodiments in which the first electrode 106 does not include the central opening 146, the fan length and the bridge length may be measured from a perimeter of an imaginary circle coaxial with the center axis C.

Similar to the first electrode 106, the second electrode 108 includes two or more fan portions 154 extending radially from the center axis C of the artificial muscle 100. The second electrode 108 includes substantially the same structure as the first electrode 106 and, thus, includes the same number of fan portions 154. Specifically, the second electrode 108 is illustrated as including four fan portions 154. However, it should be appreciated that the second electrode 108 may include any suitable number of fan portions 154.

Each fan portion 154 of the second electrode 108 has a first side edge 154*a* and an opposite second side edge 154*b*. As shown, the second terminal 152 extends from the second end 158 of one of the fan portions 154 and is integrally formed therewith. A channel 155 is at least partially defined by opposing side edges 154*a*, 154*b* of adjacent fan portions 154 and, thus, extends radially toward the center axis C. The channel 155 terminates at an end 162*a* of a bridge portion 162 interconnecting adjacent fan portions 154.

As shown in FIG. 1, additional dividing lines D are included to depict the boundary between the fan portions 154 and the bridge portions 162. The dividing lines D extend from the side edges 154*a*, 154*b* of the fan portions 154 to the first end 156 of the fan portions 154 collinear with the side edges 154*a*, 154*b*. It should be understood that dividing lines D are shown in FIG. 1 for clarity and that the fan portions 154 are integral with the bridge portions 162. The first end 156 of the fan portion 154, which extends between adjacent bridge portions 162, defines an inner length of the fan portion 154. Due to the geometry of the fan portion 154 tapering toward the center axis C between the first side edge 154*a* and the second side edge 154*b*, the second end 158 of the fan portion 154 defines an outer length of the fan portion 154 that is greater than the inner length of the fan portion 154.

Moreover, each fan portion 154 has a pair of corners 154*c* defined by an intersection of the second end 158 and each of the first side edge 154*a* and the second side edge 154*b* of the fan portion 154. In embodiments, the corners 154*c* are formed at an angle equal to or less than 90 degrees. In other embodiments, the corners 154*c* are formed at an acute angle. As described in more detail herein, during actuation of the artificial muscle 100, the corners 132*c* of the first electrode 106 and the corners 154*c* of the second electrode 108 are configured to be attracted to one another at a lower voltage as compared to the rest of the first electrode 106 and the second electrode 108. Thus, actuation of the artificial muscle 100 initially at the corners 132*c*, 154*c* results the outer perimeter 138 of the first electrode 106 and the outer perimeter 160 of the second electrode 108 being attracted to one another at a lower voltage and reducing the likelihood of air pockets or voids forming between the first electrode 106 and the second electrode 108 after actuation of the artificial muscle 100.

As shown in FIGS. 1 and 2, in embodiments, the first side edge 154*a* of each fan portion 154 has a first side length defined by a distance between the first end 156 of the fan portion 154 and the second end 158 of the fan portion 154 along the first side edge 154*a* and the dividing line D that is collinear with the first side edge 154*a*. Each fan portion 154 also has a second side length defined by a distance between the first end 156 of the fan portion 154 and the second end 158 of the fan portion 154 along the second side edge 154*b* and the dividing line D that is collinear with the second side edge 154*b*. In embodiments, the first side length is greater than the second side length of the fan portion 154 such that the second electrode 108 has an ellipsoid geometry corresponding to the geometry of the first electrode 106.

The second end 158, the first side edge 154*a* and the second side edge 154*b* of each fan portion 154, and the bridge portions 162 interconnecting the fan portions 154 define an outer perimeter 160 of the second electrode 108. In embodiments, a central opening 168 is formed within the second electrode 108 between the fan portions 154 and the bridge portions 162, and is coaxial with the center axis C. Each fan portion 154 has a fan length extending from a perimeter 164 of the central opening 168 to the second end 158 of the fan portion 154. Each bridge portion 162 has a bridge length extending from the central opening 168 to the end 162*a* of the bridge portion 162, i.e., the channel 155. As shown, the bridge length of each of the bridge portions 162 is substantially equal to one another. Each channel 155 has a channel length defined by a distance between the end 162*a* of the bridge portion 162 and the second end of the fan portion 154. Due to the bridge length of each of the bridge portions 162 being substantially equal to one another and the first side length of the fan portions 154 being greater than the second side length of the fan portions 154, a first pair of opposite channels 155 has a channel length greater than a channel length of a second pair of opposite channels 155. As shown, a width of the channel 155 extending between opposing side edges 154*a*, 154*b* of adjacent fan portions 154 remains substantially constant due to opposing side edges 154*a*, 154*b* being substantially parallel to one another.

In embodiments, the central opening 168 has a radius of 2 cm to 5 cm. In embodiments, the central opening 168 has a radius of 3 cm to 4 cm. In embodiments, a total fan area of each of the fan portions 154 is equal to or greater than twice an area of the central opening 168. It should be appreciated that the ratio between the total fan area of the fan portions 154 and the area of the central opening 168 is directly related to a total amount of deflection of the second film layer 124 when the artificial muscle 100 is actuated. In embodiments, the bridge length is 20% to 50% of the fan length. In embodiments, the bridge length is 30% to 40% of the fan length. In embodiments in which the second electrode 108 does not include the central opening 168, the fan length and the bridge length may be measured from a perimeter of an imaginary circle coaxial with the center axis C.

As described herein, the first electrode 106 and the second electrode 108 each have a central opening 146, 168 coaxial with the center axis C. However, it should be understood that the first electrode 106 does not need to include the central opening 146 when the central opening 168 is provided within the second electrode 108. Alternatively, the second electrode 108 does not need to include the central opening 168 when the central opening 146 is provided within the first electrode 106.

Referring again to FIG. 1, the electrical insulator membrane 110 may have a substantially ellipsoid geometry generally corresponding to the geometry of the first electrode 106 and the second electrode 108. Thus, the electrical insulator membrane 110 may have fan portions 172 and bridge portions 176 corresponding to like portions on the first electrode 106 and the second electrode 108. Further, the electrical insulator membrane 110 has an outer perimeter 180 corresponding to the outer perimeter 138 of the first electrode 106 and the outer perimeter 160 of the second electrode 108, respectively, when positioned thereon. In embodiments, the electrical insulator membrane 110 may extend across the central opening 146, 168 of the first electrode 106 and the second electrode 108. In other embodiments, the electrical insulator membrane 110 may also have a central opening formed therein and coaxial with the central opening 146, 168 of the first electrode 106 and the second electrode 108. Additionally, the electrical insulator membrane 110 may completely isolate the second electrode 108, or in embodiments, the first electrode 106, from a dielectric fluid 198.

In embodiments, the electrical insulator membrane 110 includes an adhesive surface 184 and an opposite non-sealable surface 188. Thus, in embodiments, the electrical insulator membrane 110 is a polymer tape adhered to the inner surface 150 of the second electrode 108. In embodiments, the electrical insulator membrane 110 comprises BOPP.

Figure 3:
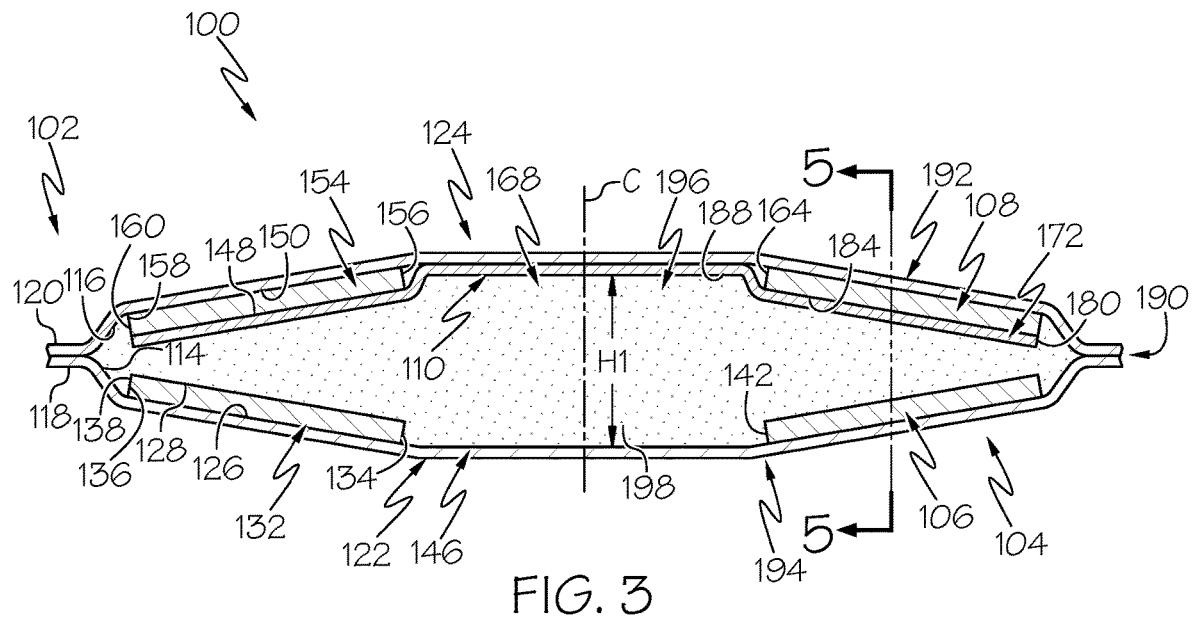
FIG. 3 schematically depicts a cross-sectional view of the artificial muscle of FIG. 1 taken along line 3-3 in FIG. 2 in a non-actuated state, according to one or more embodiments shown and described herein.
Figure 4:
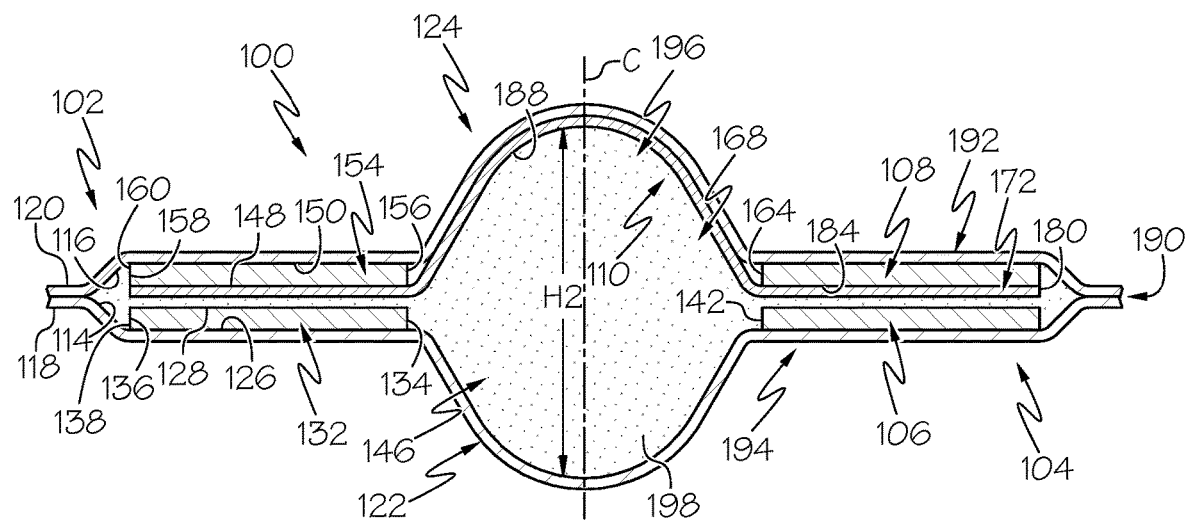
FIG. 4 schematically depicts a cross-sectional view of the artificial muscle of FIG. 3 in an actuated state, according to one or more embodiments shown and described herein.

Referring now to FIGS. 2-4, the artificial muscle 100 is shown in its assembled form with the first terminal 130 of the first electrode 106 and the second terminal 152 of the second electrode 108 extending past an outer perimeter of the housing 102, i.e., the first film layer 122 and the second film layer 124. As shown in FIG. 2, the second electrode 108 is stacked on top of the first electrode 106 and, therefore, the first electrode 106, the first film layer 122, and the second film layer 124 are not shown. In its assembled form, the first electrode 106, the second electrode 108, and the electrical insulator membrane 110 are sandwiched between the first film layer 122 and the second film layer 124. The first film layer 122 is partially sealed to the second film layer 124 at an area surrounding the outer perimeter 138 of the first electrode 106 and the outer perimeter 160 of the second electrode 108. In some embodiments, the first film layer 122 is heat-sealed to the second film layer 124. Specifically, in some embodiments, the first film layer 122 is sealed to the second film layer 124 to define a sealed portion 190 surrounding the first electrode 106 and the second electrode 108. The first film layer 122 and the second film layer 124 may be sealed in any suitable manner, such as using an adhesive, heat sealing, vacuum sealing, or the like.

The first electrode 106, the second electrode 108, and the electrical insulator membrane 110 provide a barrier that prevents the first film layer 122 from sealing to the second film layer 124 forming an unsealed portion 192. The unsealed portion 192 of the housing 102 includes an electrode region 194, in which the electrode pair 104 is provided, and an expandable fluid region 196, which is surrounded by the electrode region 194. The central openings 146, 168 of the first electrode 106 and the second electrode 108 define the expandable fluid region 196 and are arranged to be axially stacked on one another. Although not shown, the housing 102 may be cut to conform to the geometry of the electrode pair 104 and reduce the size of the artificial muscle 100, namely, the size of the sealed portion 190.

A dielectric fluid 198 is provided within the unsealed portion 192 and flows freely between the first electrode 106 and the second electrode 108. A "dielectric" fluid as used herein is a medium or material that transmits electrical force without conduction and as such has low electrical conductivity. Some non-limiting example dielectric fluids include perfluoroalkanes, transformer oils, and deionized water. It should be appreciated that the dielectric fluid 198 may be injected into the unsealed portion 192 of the artificial muscle 100 using a needle or other suitable injection device.

Referring now to FIGS. 3 and 4, the artificial muscle 100 is actuatable between a non-actuated state and an actuated state. In the non-actuated state, as shown in FIG. 3, the first electrode 106 and the second electrode 108 are partially spaced apart from one another proximate the central openings 146, 168 thereof and the first end 134, 156 of the fan portions 132, 154. The second end 136, 158 of the fan portions 132, 154 remain in position relative to one another due to the housing 102 being sealed at the outer perimeter 138 of the first electrode 106 and the outer perimeter 160 of the second electrode 108. In the actuated state, as shown in FIG. 4, the first electrode 106 and the second electrode 108 are brought into contact with and oriented parallel to one another to force the dielectric fluid 198 into the expandable fluid region 196. This causes the dielectric fluid 198 to flow through the central openings 146, 168 of the first electrode 106 and the second electrode 108 and inflate the expandable fluid region 196.

Referring now to FIG. 3, the artificial muscle 100 is shown in the non-actuated state. The electrode pair 104 is provided within the electrode region 194 of the unsealed portion 192 of the housing 102. The central opening 146 of the first electrode 106 and the central opening 168 of the second electrode 108 are coaxially aligned within the expandable fluid region 196. As such, the central openings 146, 168 encircle and define the expandable fluid region 196. In the non-actuated state, the first electrode 106 and the second electrode 108 are partially spaced apart from and non-parallel to one another. Due to the first film layer 122 being sealed to the second film layer 124 around the electrode pair 104, the second end 136, 158 of the fan portions 132, 154 are brought into contact with one another. Thus, dielectric fluid 198 is provided between the first electrode 106 and the second electrode 108, thereby separating the first end 134, 156 of the fan portions 132, 154 proximate the expandable fluid region 196. Stated another way, a distance between the first end 134 of the fan portion 132 of the first electrode 106 and the first end 156 of the fan portion 154 of the second electrode 108 is greater than a distance between the second end 136 of the fan portion 132 of the first electrode 106 and the second end 158 of the fan portion 154 of the second electrode 108. This results in the electrode pair 104 zippering toward the expandable fluid region 196 when actuated. More particularly, zippering of the electrode pair 104 is initiated at the corners 132c of the first electrode 106 and the corners 154c of the second electrode 108, as discussed herein. In some embodiments, the first electrode 106 and the second electrode 108 may be flexible. Thus, as shown in FIG. 3, the first electrode 106 and the second electrode 108 are convex such that the second ends 136, 158 of the fan portions 132, 154 thereof may remain close to one another, but spaced apart from one another proximate the central openings 146, 168. In the non-actuated state, the expandable fluid region 196 has a first height H1.

When actuated, as shown in FIG. 4, the first electrode 106 and the second electrode 108 zipper toward one another from the second ends 136, 158 of the fan portions 132, 154 thereof, thereby pushing the dielectric fluid 198 into the expandable fluid region 196. As shown, when in the actuated state, the first electrode 106 and the second electrode 108 are parallel to one another. In the actuated state, the dielectric fluid 198 flows into the expandable fluid region 196 to inflate the expandable fluid region 196. As such, the first film layer 122 and the second film layer 124 expand in opposite directions. In the actuated state, the expandable fluid region 196 has a second height H2, which is greater than the first height H1 of the expandable fluid region 196 when in the non-actuated state. Although not shown, it should be noted that the electrode pair 104 may be partially actuated to a position between the non-actuated state and the actuated state. This would allow for partial inflation of the expandable fluid region 196 and adjustments when necessary.

In order to move the first electrode 106 and the second electrode 108 toward one another, a voltage is applied by a power supply, such as the power supply 406 (FIG. 9). In some embodiments, a voltage of up to 10 kV may be provided from the power supply to induce an electric field through the dielectric fluid 198. The resulting attraction between the first electrode 106 and the second electrode 108 pushes the dielectric fluid 198 into the expandable fluid region 196. Pressure from the dielectric fluid 198 within the expandable fluid region 196 causes the first film layer 122 to deform in a first axial direction along the center axis C of the first electrode 106 and causes the second film layer 124 and the electrical insulator membrane 110 to deform in an opposite second axial direction along the center axis C of the second electrode 108. Once the voltage being supplied to the first electrode 106 and the second electrode 108 is discontinued, the first electrode 106 and the second electrode 108 return to their initial, non-parallel position in the non-actuated state.

It should be appreciated that the present embodiments disclosed herein, specifically, the fan portions 132, 154 with the interconnecting bridge portions 140, 162, provide a number of improvements over actuators, such as HASEL actuators, that do not include the fan portions 132, 154. Embodiments of the artificial muscle 100 including fan portions 132, 154 on each of the first electrode 106 and the second electrode 108, respectively, increases the surface area and, thus, displacement at the expandable fluid region 196 without increasing the amount of voltage required as compared to known HASEL actuators including donut-shaped electrodes having a uniform, radially-extending width. In addition, the corners 132c, 154c of the fan portions 132, 154 of the artificial muscle 100 provide zipping fronts that result in focused and directed zipping along the outer perimeters 138, 160 of the first electrode 106 and the second electrode 108 during actuation as compared to HASEL actuators including donut-shaped electrodes.

Specifically, one pair of fan portions 132, 154 provides at least twice the amount of actuator power per unit volume as compared to donut-shaped HASEL actuators, while two pairs of fan portions 132, 154 provide at least four times the amount of actuator power per unit volume. The bridge portions 140, 162 interconnecting the fan portions 132, 154 also limit buckling of the fan portions 132, 154 by maintaining the distance between the channels 133, 155 and the central openings 146, 168. Because the bridge portions 140, 162 are integrally formed with the fan portions 132, 154, the bridge portions 140, 162 also prevent tearing and leakage between the fan portions 132, 154 by eliminating attachment locations that provide an increased risk of rupturing.

In operation, when the artificial muscle 100 is actuated, expansion of the expandable fluid region 196 produces a force of 20 Newton-millimeters (N·mm) per cubic centimeter ($cm^3$) of actuator volume or greater, such as 25 N·mm per $cm^3$ or greater, 30 N·mm per $cm^3$ or greater, 35 N·mm per $cm^3$ or greater, 40 N·mm per $cm^3$ or greater, or the like. In one example, when the artificial muscle 100 is actuated by a voltage of 9.5 kilovolts (kV), the artificial muscle 100 provides a resulting force of 20 N.

Moreover, the size of the first electrode 106 and the second electrode 108 is proportional to the amount of displacement of the dielectric fluid 198. Therefore, when greater displacement within the expandable fluid region 196 is desired, the size of the electrode pair 104 is increased relative to the size of the expandable fluid region 196. It should be appreciated that the size of the expandable fluid region 196 is defined by the central openings 146, 168 in the first electrode 106 and the second electrode 108. Thus, the degree of displacement within the expandable fluid region 196 may alternatively, or in addition, be controlled by increasing or reducing the size of the central openings 146, 168.

Figure 5:
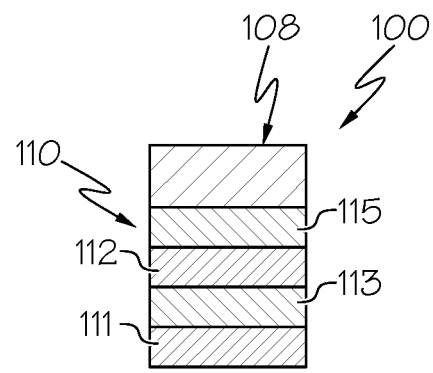
FIG. 5 schematically depicts an enlarged cross-sectional view of the artificial muscle of FIG. 1 taken along line 5-5 in FIG. 3, according to one or more embodiments shown and described herein.
Figure 5:
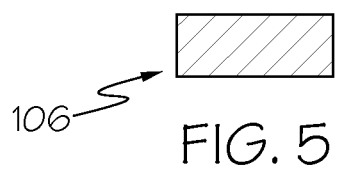

Referring now to FIG. 5, a cross-sectional view of the artificial muscle 100 is depicted taken along line 5-5 in FIG. 3. As shown in FIG. 5, the electrical insulator membrane 110 is depicted in greater detail illustrating a plurality of individual layers. More particularly, in embodiments, the electrical insulator membrane 110 includes a pair of electrical insulator layers, such as a first electrical insulator layer 111 and a second electrical insulator layer 112, a first adhesive layer 113 provided between the first electrical insulator layer 111 and the second electrical insulator layer 112, and a second adhesive layer 115 provided between the second electrical insulator layer 112 and the second electrode 108. The first electrical insulator layer 111 and the second electrical insulator layer 112 may be formed from BOPP. The first adhesive layer 113 and the second adhesive layer 115 may be formed from any suitable material such as, for example, acrylic or the like.

It should be appreciated that repeated use of an artificial muscle including a non-insulated electrode electrically coupled to a positive terminal of a power supply will result in oscillating force output and a decreasing force output over time. Accordingly, the positive terminal 406A of the power supply 406 it so be electrically coupled to the insulated electrode, i.e., the second electrode 108.

Figure 6:
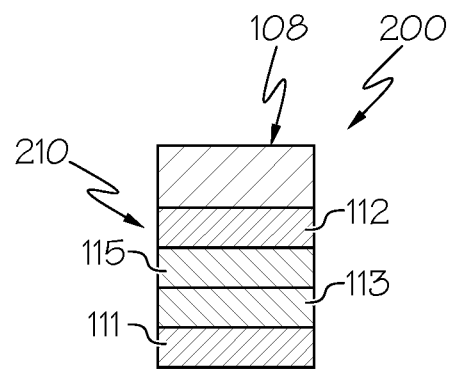
FIG. 6 schematically an enlarged cross-sectional view of an artificial muscle, according to one or more embodiments shown and described herein.
Figure 6:
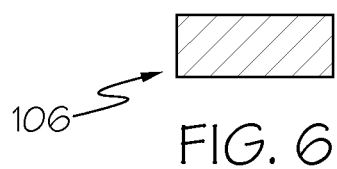

Referring now to FIG. 6, a partial cross-sectional view of an artificial muscle 200 is illustrated. It should be appreciated that the artificial muscle 200 is similar to the artificial muscle 100 and, thus, like reference numerals will be used to refer to like parts. As with the artificial muscle 100, the second electrode 108 is coated by an electrical insulator membrane 210, thereby leaving the first electrode 106 non-insulated. In embodiments, the electrical insulator membrane 210 includes a pair of electrical insulator layers, such as the first electrical insulator layer 111 and the second electrical insulator layer 112, the first adhesive layer 113, and the second adhesive layer 115. The first adhesive layer 113 and the second adhesive layer 115 are both provided between the first electrical insulator layer 111 and the second electrical insulator layer 112. Accordingly, the first adhesive layer 113 and the second adhesive layer 115 are in contact with one another and sandwiched between the first electrical insulator layer 111 and the second electrical insulator layer 112, thereby increasing a distance between the first electrical insulator layer 111 and the second electrical insulator layer 112.

It should be appreciated that the electrical insulator membranes 110, 210 illustrated in FIGS. 5 and 6, respectively, may include only a single electrical insulator layer as opposed to the pair of electrical insulator layers 111, 112. However, the pair of electrical insulator layers 111, 112 provides improved integrity and reduced likelihood of failure when one of the electrical insulator layers 111, 112 develops a defect.

Furthermore, in embodiments, it should be appreciated that each of the first electrode 106 and the second electrode 108 may include a plurality of electrode segments as opposed to a singular, integrally formed electrode extending along the entire periphery of the artificial muscle 100. In this embodiment, one or more segments of the first electrode 106 and the second electrode 108 may be insulated if one or more corresponding, opposite electrode segments of the other of the first electrode 106 and the second electrode 108 are non-insulated. However, the one or more insulated electrode segment are to be electrically coupled to the positive terminal 406A of the power supply 406 (FIG. 9) and the one or more non-insulated electrode segments are to be electrically coupled to the negative terminal 406B of the power supply 406 (FIG. 9). Additionally, it should be appreciated that any non-insulated electrode segment of one of the electrodes 106, 108 should be spaced apart from any non-insulted electrode segment of the other one of the electrodes 106, 108. Otherwise, risk of electrical arcing and failure may occur.

Figure 7:
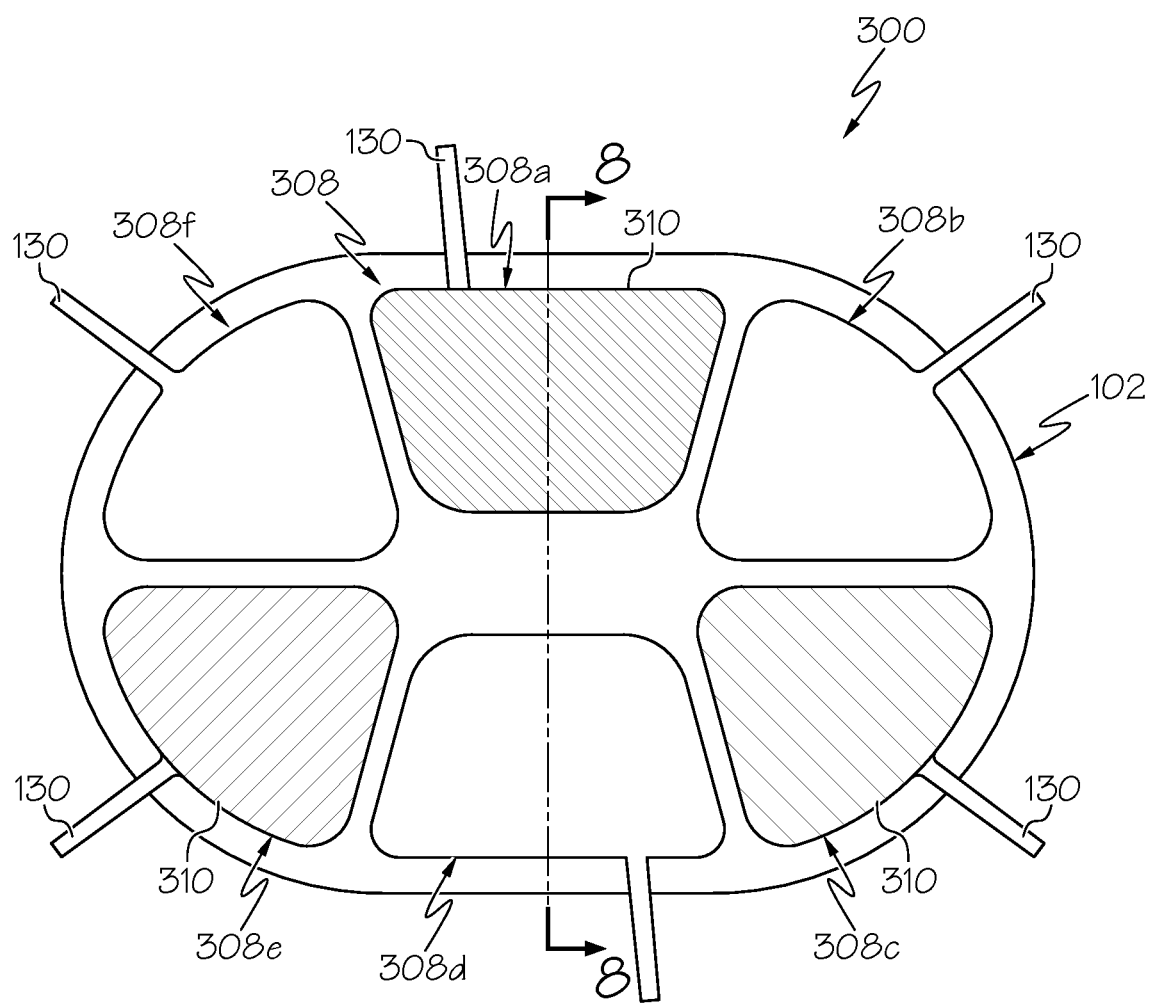
FIG. 7 schematically depicts a partial plan view of an artificial muscle, according to one or more embodiments shown and described herein.

With more particularity and referring now to FIG. 7, a partial plan view of an artificial muscle 300 is shown with certain components hidden from view. It should be appreciated that the artificial muscle 300 is similar to the artificial muscle 100 depicted herein and, thus, like reference numerals will be used to refer to like parts. Rather than the artificial muscle 300 including the first electrode 106 and the second electrode 108, each of which being a one-piece integrally formed electrode, the artificial muscle 300 includes a first electrode 306 (FIG. 8) and a second electrode 308, each including a plurality of electrode segments. For example, as shown in FIG. 7, the second electrode 308 includes a plurality of electrode segments 308a, 308b, 308c, 308d, 308e, 308f. Additionally, each of the electrode segments 308a, 308b, 308c, 308d, 308e, 308f includes a terminal 130 extending from an outer edge thereof and through the housing 102.

Referring still to FIG. 7, electrode segments 308a, 308c, 308e are provided with an electrical insulator membrane 310, such as the electrical insulator membrane 110, and the remaining electrode segments 308b, 308d, 308f are left exposed, i.e., non-insulated. It should be appreciated that the electrode segments 308a, 308b, 308c, 308d, 308e, 308f alternate between those that are electrically insulated by the electrical insulator membrane 310 and those that are not electrically insulated by the electrical insulator membrane 310. As such, the electrical insulator membrane 310 for each electrode segment 308a, 308c, 308e is separate from one another to avoid insulating adjacent electrode segments. It should be appreciated that the electrode segments 308a, 308c, 308e that are electrically insulated by the electrical insulator membrane 310 are electrically coupled to the positive terminal 406A of the power supply 406 (FIG. 9). Additionally, the electrode segments 308b, 308d, 308f that are not electrically insulated by the electrical insulator membrane 310 are electrically coupled to the negative terminal 406B of the power supply 406 (FIG. 9).

Figure 8:
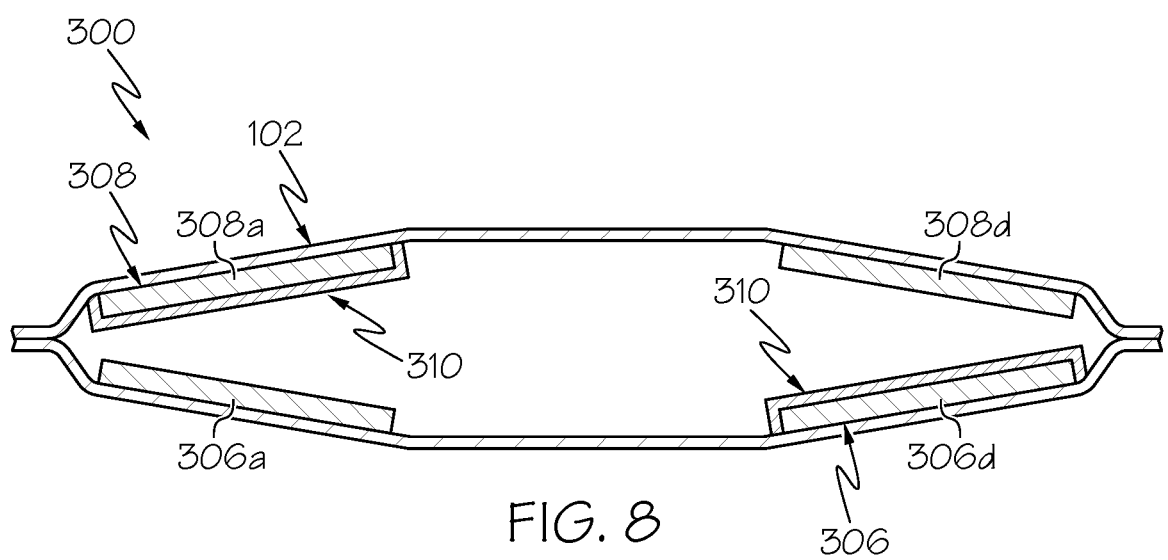
FIG. 8 schematically depicts a cross-sectional view of the artificial muscle of FIG. 7 taken along line 8-8 in FIG. 7, according to one or more embodiments shown and described herein.

Referring now to FIG. 8, a cross-sectional view of the artificial muscle 300 is illustrated. Although only a pair of electrode segments 306a, 306d of the first electrode 306 are illustrated, it should be appreciated that the first electrode 306 may be a mirror image of the second electrode 308 when positioned such that the electrode segments 306a, 306d of the first electrode 306 overlap a corresponding one of the electrode segments 308a, 308d of the second electrode 308 defining overlapping pairs of electrode segments. However, only one electrode segment of each pair of electrode segments is electrically insulated by the electrical insulator membrane 310 while the opposite electrode segment is not electrically insulated by the electrical insulator membrane 310. For example, electrode segment 308a is insulated by the electrical insulator membrane 310 while electrode segment 306a is not insulated by the electrical insulator membrane 310. Additionally, electrode segment 308d not insulated by the electrical insulator membrane 310 while electrode segment 306d is insulated by the electrical insulator membrane 310. Similar to the second electrode 308, it should be appreciated that the electrode segments 306d that is electrically insulated by the electrical insulator membrane 310 is electrically coupled to the positive terminal 406A of the power supply 406 (FIG. 9) and the electrode segment 306a that is not electrically insulated by the electrical insulator membrane 310 is electrically coupled to the negative terminal 406B of the power supply 406 (FIG. 9).

Referring now to FIG. 9, an actuation system 400 may be provided for operating an artificial muscle, such as the artificial muscles 100, 200, 300, between the non-actuated state and the actuated state. Thus, the actuation system 400 may include a controller 402, an operating device 404, a power supply 406, and a communication path 408. The various components of the actuation system 400 will now be described.

The controller 402 includes a processor 410 and a non-transitory electronic memory 412 to which various components are communicatively coupled. In some embodiments, the processor 410 and the non-transitory electronic memory 412 and/or the other components are included within a single device. In other embodiments, the processor 410 and the non-transitory electronic memory 412 and/or the other components may be distributed among multiple devices that are communicatively coupled. The controller 402 includes non-transitory electronic memory 412 that stores a set of machine-readable instructions. The processor 410 executes the machine-readable instructions stored in the non-transitory electronic memory 412. The non-transitory electronic memory 412 may comprise RAM, ROM, flash memories, hard drives, or any device capable of storing machine-readable instructions such that the machine-readable instructions can be accessed by the processor 410. Accordingly, the actuation system 400 described herein may be implemented in any conventional computer programming language, as pre-programmed hardware elements, or as a combination of hardware and software components. The non-transitory electronic memory 412 may be implemented as one memory module or a plurality of memory modules.

In some embodiments, the non-transitory electronic memory 412 includes instructions for executing the functions of the actuation system 400. The instructions may include instructions for operating the artificial muscles 100, 200, 300 based on a user command.

The processor 410 may be any device capable of executing machine-readable instructions. For example, the processor 410 may be an integrated circuit, a microchip, a computer, or any other computing device. The non-transitory electronic memory 412 and the processor 410 are coupled to the communication path 408 that provides signal interconnectivity between various components and/or modules of the actuation system 400. Accordingly, the communication path 408 may communicatively couple any number of processors with one another, and allow the modules coupled to the communication path 408 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

As schematically depicted in FIG. 9, the communication path 408 communicatively couples the processor 410 and the non-transitory electronic memory 412 of the controller 402 with a plurality of other components of the actuation system 400. For example, the actuation system 400 depicted in FIG. 9 includes the processor 410 and the non-transitory electronic memory 412 communicatively coupled with the operating device 404 and the power supply 406.

The operating device 404 allows for a user to control operation of the artificial muscles 100, 200, 300. In some embodiments, the operating device 404 may be a switch, toggle, button, or any combination of controls to provide user operation. As a non-limiting example, a user may actuate the artificial muscles 100, 200, 300 into the actuated state by activating controls of the operating device 404 to a first position. While in the first position, the artificial muscles 100, 200, 300 will remain in the actuated state. The user may switch the artificial muscles 100, 200, 300 into the non-actuated state by operating the controls of the operating device 404 out of the first position and into a second position.

The operating device 404 is coupled to the communication path 408 such that the communication path 408 communicatively couples the operating device 404 to other modules of the actuation system 400. The operating device 404 may provide a user interface for receiving user instructions as to a specific operating configuration of the artificial muscles 100, 200, 300. In addition, user instructions may include instructions to operate the artificial muscles 100, 200, 300 only at certain conditions.

The power supply 406 (e.g., battery) provides power to the artificial muscles 100, 200, 300. In some embodiments, the power supply 406 is a rechargeable direct current power source. It is to be understood that the power supply 406 may be a single power supply or battery for providing power to the artificial muscle 100, 200, 300. A power adapter (not shown) may be provided and electrically coupled via a wiring harness or the like for providing power to the artificial muscles 100, 200, 300 via the power supply 406. As discussed herein, the power supply 406 includes a positive terminal 406A and a negative terminal 406B. The positive terminal 406A is electrically coupled to the insulated electrode, or the insulated electrode segments, of the first electrode 106 and the second electrode 108 and the negative terminal 406B is electrically coupled to the non-insulated electrode, or non-insulated electrode segments, of the first electrode 106 and the second electrode 108. In the embodiments discussed herein, the positive terminal 406A is electrically coupled to the second terminal 152 of the second electrode 108 and the negative terminal 406B is electrically coupled to the first terminal 130 of the first electrode 106.

In some embodiments, the actuation system 400 also includes a display device 414. The display device 414 is coupled to the communication path 408 such that the communication path 408 communicatively couples the display device 414 to other modules of the actuation system 400. The display device 414 may output a notification in response to an actuation state of the artificial muscles 100, 200, 300 or indication of a change in the actuation state of the artificial muscles 100, 200, 300. Moreover, the display device 414 may be a touchscreen that, in addition to providing optical information, detects the presence and location of a tactile input upon a surface of or adjacent to the display device 414. Accordingly, the display device 414 may include the operating device 404 and receive mechanical input directly upon the optical output provided by the display device 414.

In some embodiments, the actuation system 400 includes network interface hardware 416 for communicatively coupling the actuation system 400 to a portable device 418 via a network 420. The portable device 418 may include, without limitation, a smartphone, a tablet, a personal media player, or any other electric device that includes wireless communication functionality. It is to be appreciated that, when provided, the portable device 418 may serve to provide user commands to the controller 402, instead of the operating device 404. As such, a user may be able to control or set a program for controlling the artificial muscles 100, 200, 300 without utilizing the controls of the operating device 404. Thus, the artificial muscles 100, 200, 300 may be controlled remotely via the portable device 418 wirelessly communicating with the controller 402 via the network 420.

From the above, it is to be appreciated that defined herein are artificial muscles for inflating or deforming a surface of an object by selectively actuating the artificial muscle to raise and lower a region thereof. This provides a low profile inflation member that may operate on demand.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An artificial muscle system comprising:
   an artificial muscle comprising:
      an electrode pair comprising a first electrode and a second electrode;
      an electrical insulator membrane fixed to a surface of the second electrode facing the first electrode, the electrical insulator membrane comprising a first electrical insulator layer and a second electrical insulator layer positioned between the first electrical insulator layer and the second electrode;
      a housing comprising an electrode region and an expandable fluid region;
      the electrode pair positioned in the electrode region of the housing; and
      a dielectric fluid housed within the housing; and
   a power supply including a positive terminal and a negative terminal, the positive terminal electrically coupled to the second electrode, the negative terminal electrically coupled to the first electrode,
   wherein the electrode pair is actuatable between a non-actuated state and an actuated state such that actuation from the non-actuated state to the actuated state directs the dielectric fluid into the expandable fluid region.

2. The artificial muscle system of claim 1, wherein the electrical insulator membrane comprises:
   a first adhesive layer positioned between the first electrical insulator layer and the second electrical insulator layer.

3. The artificial muscle system of claim 2, wherein the electrical insulator membrane comprises:
  a second adhesive layer positioned between the first electrical insulator layer and the second electrical insulator layer.

4. The artificial muscle system of claim 2, wherein the electrical insulator membrane comprises:
  a second adhesive layer positioned between the second electrical insulator layer and the second electrode.

5. The artificial muscle system of claim 1, wherein the first electrical insulator layer and the second electrical insulator layer each comprises biaxially oriented polypropylene.

6. The artificial muscle system of claim 1, wherein a surface of the first electrode is in direct contact with the dielectric fluid.

7. The artificial muscle system of claim 1, wherein the first electrode and the second electrode each comprise two or more fan portions and two or more bridge portions, wherein:
  each of the two or more bridge portions interconnects adjacent fan portions; and
  at least one of the first electrode and the second electrode comprises a central opening positioned between the two or more fan portions and encircling the expandable fluid region.

8. An artificial muscle system comprising:
  an artificial muscle comprising:
    an electrode pair comprising a first electrode and a second electrode, the first electrode and the second electrode each comprising a plurality of electrode segments;
    an electrical insulator membrane fixed to one or more insulated electrode segments of the first electrode and one or more opposite insulated electrode segments of the second electrode;
    a housing comprising an electrode region and an expandable fluid region;
    the electrode pair positioned in the electrode region of the housing, the first electrode fixed to a first surface of the housing and the second electrode fixed to a second surface of the housing; and
    a dielectric fluid housed within the housing; and
  a power supply including a positive terminal and a negative terminal, the positive terminal electrically coupled to the one or more insulated electrode segments of the first electrode and the one or more opposite insulated electrode segments of the second electrode, the negative terminal electrically coupled to one or more non-insulated electrode segments of the first electrode and one or more opposite non-insulated electrode segments of the second electrode,
  wherein the electrode pair is actuatable between a non-actuated state and an actuated state such that actuation from the non-actuated state to the actuated state directs the dielectric fluid into the expandable fluid region.

9. The artificial muscle system of claim 8, wherein the electrical insulator membrane is not fixed to the one or more non-insulated electrode segments of the first electrode and the one or more non-insulated electrode segments of the second electrode.

10. The artificial muscle system of claim 8, wherein the one or more insulated electrode segments of the first electrode and the one or more insulated electrode segments of the second electrode are spaced apart from one another by the one or more non-insulated electrode segments of the first electrode and the one or more non-insulated electrode segments of the second electrode, respectively.

11. The artificial muscle system of claim 9, wherein the electrical insulator membrane comprises:
  a first electrical insulator layer; and
  a second electrical insulator layer positioned between the first electrical insulator layer and the second electrode.

12. The artificial muscle system of claim 11, wherein the electrical insulator membrane comprises:
  a first adhesive layer positioned between the first electrical insulator layer and the second electrical insulator layer.

13. The artificial muscle system of claim 12, wherein the electrical insulator membrane comprises:
  a second adhesive layer positioned between the first electrical insulator layer and the second electrical insulator layer.

14. The artificial muscle system of claim 12, wherein the electrical insulator membrane comprises:
  a second adhesive layer positioned between the second electrical insulator layer and the second electrode.

15. The artificial muscle system of claim 11, wherein the first electrical insulator layer and the second electrical insulator layer each comprises biaxially oriented polypropylene.

16. A method for actuating an artificial muscle, the method comprising:
  electrically coupling a negative terminal and a positive terminal of a power supply to an electrode pair of the artificial muscle, the artificial muscle comprising:
    a housing having an electrode region and an expandable fluid region;
    the electrode pair comprising a first electrode electrically coupled to the negative terminal of the power supply, and a second electrode electrically coupled to the positive terminal of the power supply, the electrode pair positioned in the electrode region of the housing; and
    an electrical insulator membrane fixed to the second electrode, the electrical insulator membrane comprising a first electrical insulator layer and a second electrical insulator layer positioned between the first electrical insulator layer and the second electrode; and
  applying a voltage from the power supply to the electrode pair of the artificial muscle, thereby actuating the electrode pair from a non-actuated state to an actuated state such that dielectric fluid is directed into the expandable fluid region of the housing and expands the expandable fluid region.

17. The method of claim 16, wherein the electrical insulator membrane is fixed to a surface of the second electrode facing the first electrode.

18. The method of claim 17, wherein a surface of the first electrode is in direct contact with the dielectric fluid.

19. The method of claim 16, wherein the first electrode and the second electrode each comprise two or more fan portions and two or more bridge portions, wherein:
  each of the two or more bridge portions interconnects adjacent fan portions; and
  at least one of the first electrode and the second electrode comprises a central opening positioned between the two or more fan portions and encircling the expandable fluid region.

* * * * *

UNITED STATES PATENT AND TRADEMARK OFFICE
CERTIFICATE OF CORRECTION

| | |
|---|---|
| PATENT NO. | : 12,403,588 B2 |
| APPLICATION NO. | : 17/685504 |
| DATED | : September 2, 2025 |
| INVENTOR(S) | : Maduran Palaniswamy, Michael P. Rowe and Max P. Herzog |

It is certified that error appears in the above-identified patent and that said Letters Patent is hereby corrected as shown below:

In the Specification

In Column 5, Line(s) 21, delete "in in" and insert --in--, therefor.

Signed and Sealed this
Fourteenth Day of October, 2025

John A. Squires
*Director of the United States Patent and Trademark Office*